United States Patent [19]

Kovacevic et al.

[11] Patent Number: 5,027,828
[45] Date of Patent: Jul. 2, 1991

[54] SENSORY DISCRIMINATOR HAVING BODY-CONTACTING PRONGS

[75] Inventors: Nebojsa Kovacevic, Plymouth, Minn.; A. Lee Dellon, Baltimore, Md.

[73] Assignee: N. K. Biotechnical Engineering Company, Minneapolis, Minn.

[21] Appl. No.: 439,651

[22] Filed: Nov. 21, 1989

[51] Int. Cl.[5] .............................................. A61B 5/103
[52] U.S. Cl. .................................... 128/774; 128/739; 128/740; 128/744; 606/204; 73/781
[58] Field of Search ............................. 128/41, 739–742, 128/744, 782, 774, 419 S, 419 C; 606/201, 204; 73/781, 81

[56] References Cited

U.S. PATENT DOCUMENTS

| | | | |
|---|---|---|---|
| 2,625,152 | 1/1953 | Frohring | 128/2 |
| 3,782,365 | 1/1974 | Pinna | 73/81 |
| 3,933,148 | 1/1976 | Wyler et al. | 128/2 R |
| 3,937,212 | 2/1976 | Fletcher et al. | 128/782 |
| 4,058,005 | 11/1977 | Barnett | 73/781 |
| 4,132,224 | 1/1979 | Randolph | 128/774 |
| 4,217,912 | 8/1980 | Hubmann et al. | 128/744 |
| 4,249,417 | 2/1981 | Feldstein et al. | 128/774 |
| 4,250,891 | 2/1981 | Carlson et al. | 128/744 |
| 4,313,446 | 2/1982 | Kanatani | 128/744 |
| 4,641,661 | 2/1987 | Kalarickal | 128/744 |
| 4,763,666 | 8/1988 | Strian et al. | 128/742 |

OTHER PUBLICATIONS

Hasin et al., "Miniature Force Transducer for Myocardial Stimulation & Local Tension Measurements", pp. 104, 105.
Byrne, "A Feedback Controlled Stimulator that Delivers Controlled Displacements or Forces to Cutaneous Mechanoreceptors", pp. 66–68.
A. Lee Dellon, M.D., "Evaluation of Sensibility of Sensation in the Hand", pp. 28–31.

Primary Examiner—Max Hindenburg
Assistant Examiner—Robin R. Longo
Attorney, Agent, or Firm—Kinney & Lange

[57] ABSTRACT

A sensing device for determining the sensory responses of the human skin to evaluate the fiber-receptor nervous system of the human body, primarily in connection with the measurement of the ability to discriminate separate points of touch of the hand. The sensing device includes electronic sensors for determining the displacement, or force, acting on individually mounted prongs or pins which are positioned to engage and apply a load to a human body. The force sensors provide not only the load individually to each of the prongs, but also the average load applied to the surface of the human body by the two prongs.

8 Claims, 4 Drawing Sheets

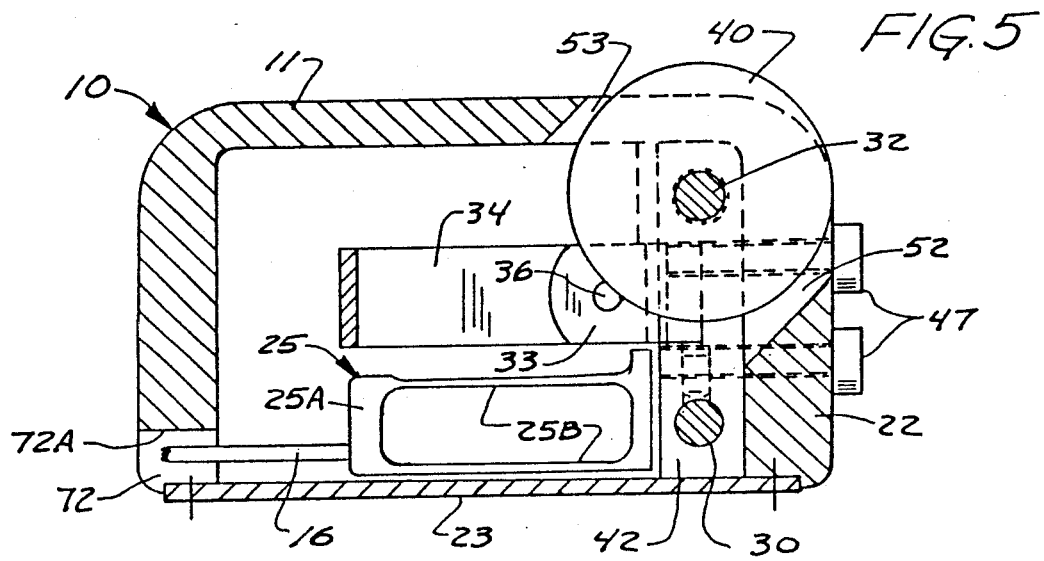
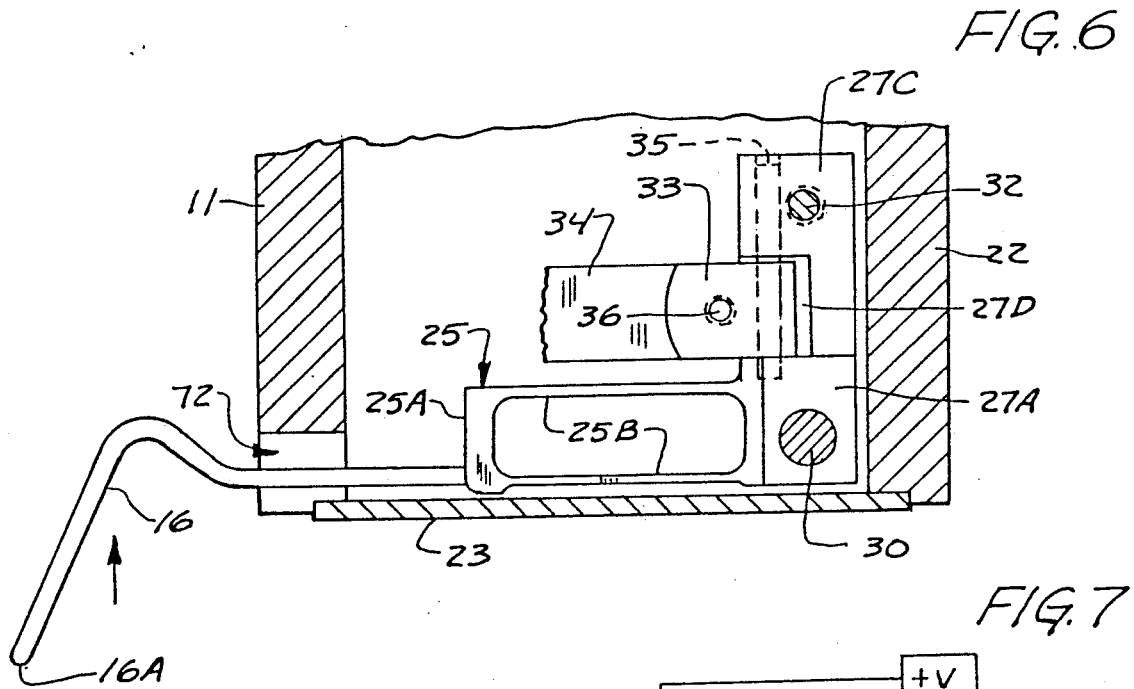
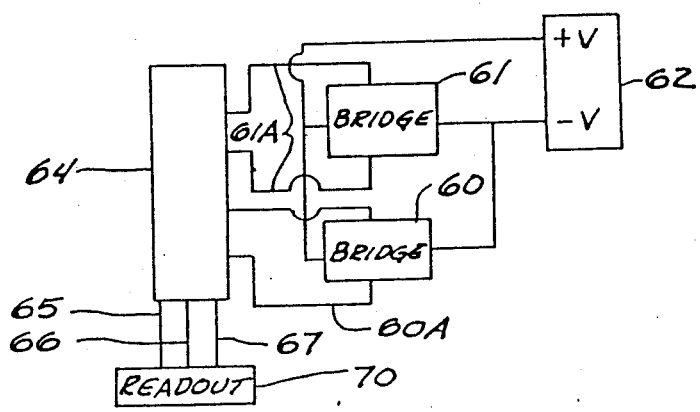

SENSORY DISCRIMINATOR HAVING BODY-CONTACTING PRONGS

BACKGROUND OF THE INVENTION

The present invention relates to a device for measuring the ability to identify the level at which a finger or other portion of the hand or foot senses and identifies stimulation from two points. The purpose of the test is to determine the innervation density of the patient's fiber-receptor system in the area tested. When the points are moved across the surface of the skin, the quickly adapting fiber-receptor system responds. The moving test will assess hand functions requiring moving touch, such as object identification, buttoning a button or the like. A static two point discrimination test, that is when two points are pressed against a portion of the hand, tests the slowly adapting fiber-receptor system. The static test will assess hand functions requiring a sensory grip and constant touch, such as holding tools, pencils or the like.

It has been well known to provide one or two point discrimination tests. A device known as the DISK-CRIMINATOR has been advanced, and it comprises a round disk that has a series of metal rods or prongs protruding from the periphery at different spacings, and then the rods or prongs are either individually pressed onto a test point, or two adjacent ones are pressed onto a test point for the testing. The measurements with the prior art device are quite subjective, and the need for precision measurement of the force at which the sensory system of the hand responds exists.

SUMMARY OF THE INVENTION

The present invention provides a sensing device that has a housing which mounts at least one probe or prong through a load sensing system, and permits an operator to apply load through one or two prongs onto the surface of the skin of a patient to determine sensory responses. As shown, suitable force sensing devices are used for determining the displacement, or the force on each of two prongs or pins, as well as selectively providing the average load applied to the surface of the human body through both of the prongs. The output is used for comparative purposes for analyzing the innervation density, either of the quickly adapting fibers-receptor system using a moving motion of the prongs, or of the slowly adapting fiber-receptor system when a static load is applied.

The present sensing device permits adjustment of the spacing between two prongs to provide a range of tests, and can be used to measure force across the desired range of loading for normal patient evaluation.

Additionally, there are mechanical overload stops provided to limit travel of the prongs to avoid damaging sensitive electronic sensors. The sensors are easily used in connection with known readout equipment.

The ability to measure the force at which sensory perception occurs, either when moving the prongs or under static tests, greatly aids in determining the progress of rehabilitation.

The ability to determine the force permits an examiner or physical therapist to know where the patient's discrimination level is, and aids in repeat and comparative testing. The present device is useful for measuring the innervation density of any surface area, not just the finger tip. It also may be used for determining rate o restoration of touch sensing after a nerve injury and nerve repair. It can be used for testing areas of skin before and after transfer to resurface or reconstruct other areas of the body. In the learning process, also, for example after injury, a patient can learn to distinguish the presence of any stimulus within a particular force range, and can start with the prongs spaced far apart so that two separate stimuli are more easily identified. The patient can attempt to distinguish the difference between one or two points moving along the finger. The patient may not initially recognize the two prongs as two separate stimuli, but may be able to perceive that the two points feel "different" than one point. Recognizing two point stimuli is easier with the pins spaced far apart, so initial recognition will start with a wide spacing. Then, through a learning process the recognition of two point stimuli will occur with the prongs spaced at narrowed spacings.

The device shown is easily adapted to a wide range of therapeutic uses, and is rugged, easy to use and makes the analysis of sensory perception more precise because of the ability to measure the force applied by the discriminator prongs.

BRIEF DESCRIPTION OF THE DRAWINGS

FIG. 5 is a sectional view taken as on line 5—5 in FIG. 4;

FIG. 6 is a sectional view taken as on line 6—6 in FIG. 4; and

FIG. 7 is a simplified schematic block diagram of a typical circuit used with the sensor of the present invention.

DETAILED DESCRIPTION OF THE PREFERRED EMBODIMENTS

Figure 1:
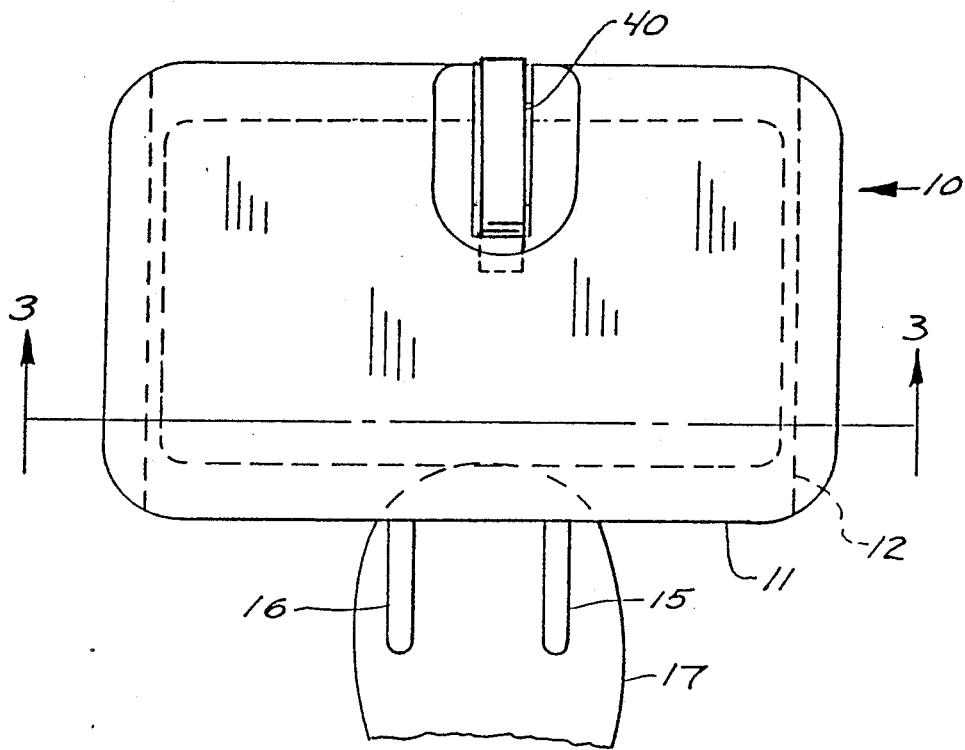
FIG. 1 is a top plan view of the case of a sensing device made according to the present invention.
Figure 2:
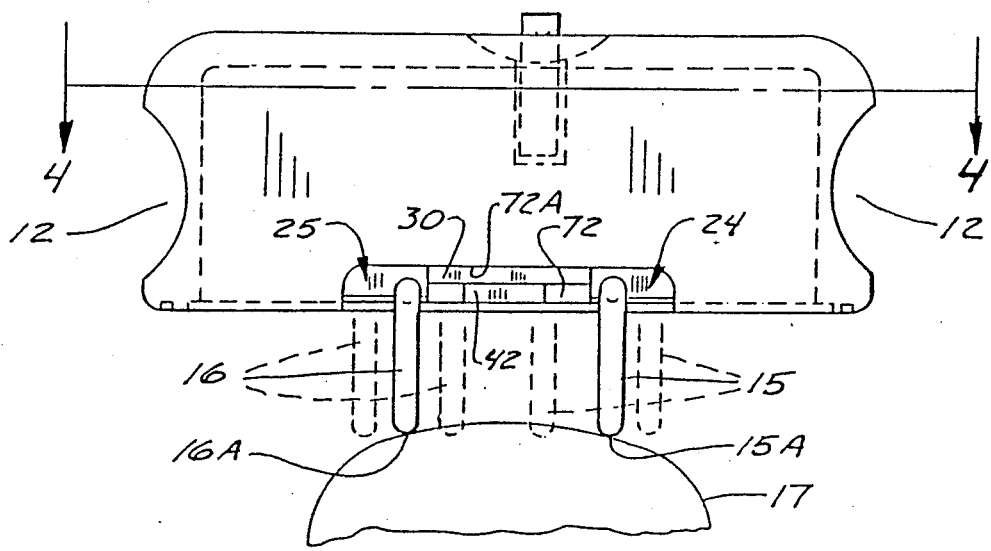
FIG. 2 is a side elevational view thereof showing the prongs that are used for the testing in position.

In FIG. 1, a sensing device made according to the present invention is indicated generally at 10 and includes an outer case 11 that is easily held in one hand, and which has side grooves indicated at 12 and 13, formed on the opposite side edges thereof (see FIG. 2) for easy grasping. The case has rounded edges to avoid any injuries or the like. The device is used for analyzing the sensory responses of the skin of a person, primarily of the hand, and specifically for conducting sensory discrimination tests which evaluate the ability of a patient to discriminate between stimuli from a single point and/or two spaced points. The case 10 thus carries first and second prongs or pins 15 and 16, respectively, which are mounted relative to the case through load sensing flexure assemblies that permit measuring the force applied to the outer ends 15A and 16A of the prongs. The outer ends 15A and 16A are shown in FIG. 2, pressing against the surface 17 of a finger that is shown only schematically. The prongs 15 and 16 are laterally adjustable, as shown by the dotted lines in FIG. 2.

Referring specifically to FIGS. 3 through 6, the inner mechanical construction of the present device is illustrated. The outer case 11 has a continuous top wall 20, end walls 21, and side walls 22. The case 11 has an open bottom aperture that is covered with a cover plate 23 that is held in place with suitable screws. The prongs or pins 15 and 16 are mounted on separate flexure assemblies 24 and 25, respectively, which are mirror images of each other, and each flexure assembly has an outer end wall 24A and 25A, respectively, to which one end of the respective prong 15 and 16 is threadably attached. The walls 24A and 25A are mounted on repeated pairs of flexure straps 24B, 24B and 25B, 25B, respectively. The flexure straps of each pair are spaced in vertical direction (the direction of force application) and are mounted back onto slide and adjustment blocks 26 and 27, respectively. The slide and adjustment blocks have lower journals 26A and 27A which is slidably mounted onto a transverse guide shaft 30.

Additionally, the slide and adjustment blocks have upright columns 26B and 27B, respectively, integral with the lower journals 26A and 27A. The upper ends of the columns 26B and 27B have head members 26C and 27C that have transverse threaded openings that are of size to receive a generally horizontal adjustment screw 32, which is parallel to the guide shaft 30. The columns 26B and 27B also have recessed portions in the midsection shown at 26D and 27D, (below the head portions and above the journals), respectively, and these recessed portions are used for mounting pivot brackets shown at 33 which in turn support ends of a formed flat spring 34. The spring 34 is used to create a force tending to urge the two slide and adjustment blocks 26 and 27 toward each other, and thus toward the center of the case or housing.

The pivot members 33 are pivotally held in their respective recess 26D and 27D with pivot pins 34 that pass through vertical openings in the respective head members 26C and 27C. The head member 27C is broken away in FIG. 3 to show the pivot pin 34 in position. The pivot members 33 are bifurcated or split, or in other words form grooves which receive end portions of the spring 34, and screws 36 are used for clamping the ends of the spring in position on the pivot members. The spring 34 is a bowed spring that is formed as shown in FIG. 4 and is made so that it has to be sprung apart to be mounted as shown in FIG. 4 and it will urge the slide and adjustment blocks 26 and 27 inwardly.

The threaded screw 32 has a thumb wheel 40. The thumb wheel 40 will permit rotating the screw 32 for moving the slide and adjustment blocks 26 and 27 along the guide shaft 30. Both the screw 32 and the guide shaft 30 are supported in a support block 42, which has a hub portion 43 at the lower portion thereof, near the cover plate 23. Hub portion 43 has a bore 44 for receiving the guide shaft. A suitable set screw 45 is mounted in a threaded opening in the hub portion 43 and engages a lock groove in the shaft 30 to hold the shaft from sliding axially or from rotating.

Figure 3:
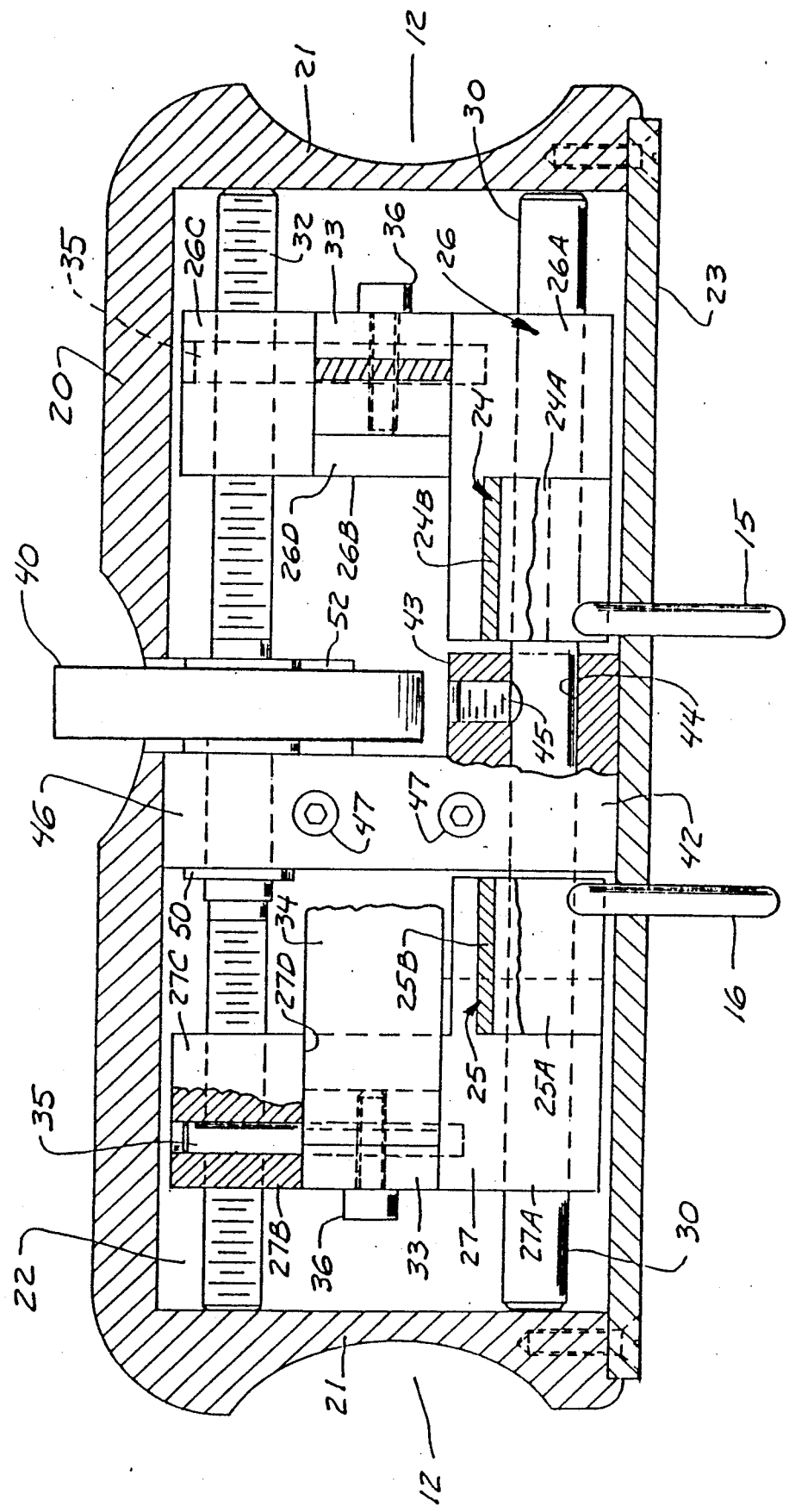
FIG. 3 is an enlarged sectional view taken as on line 3—3 in FIG. 1.
Figure 4:
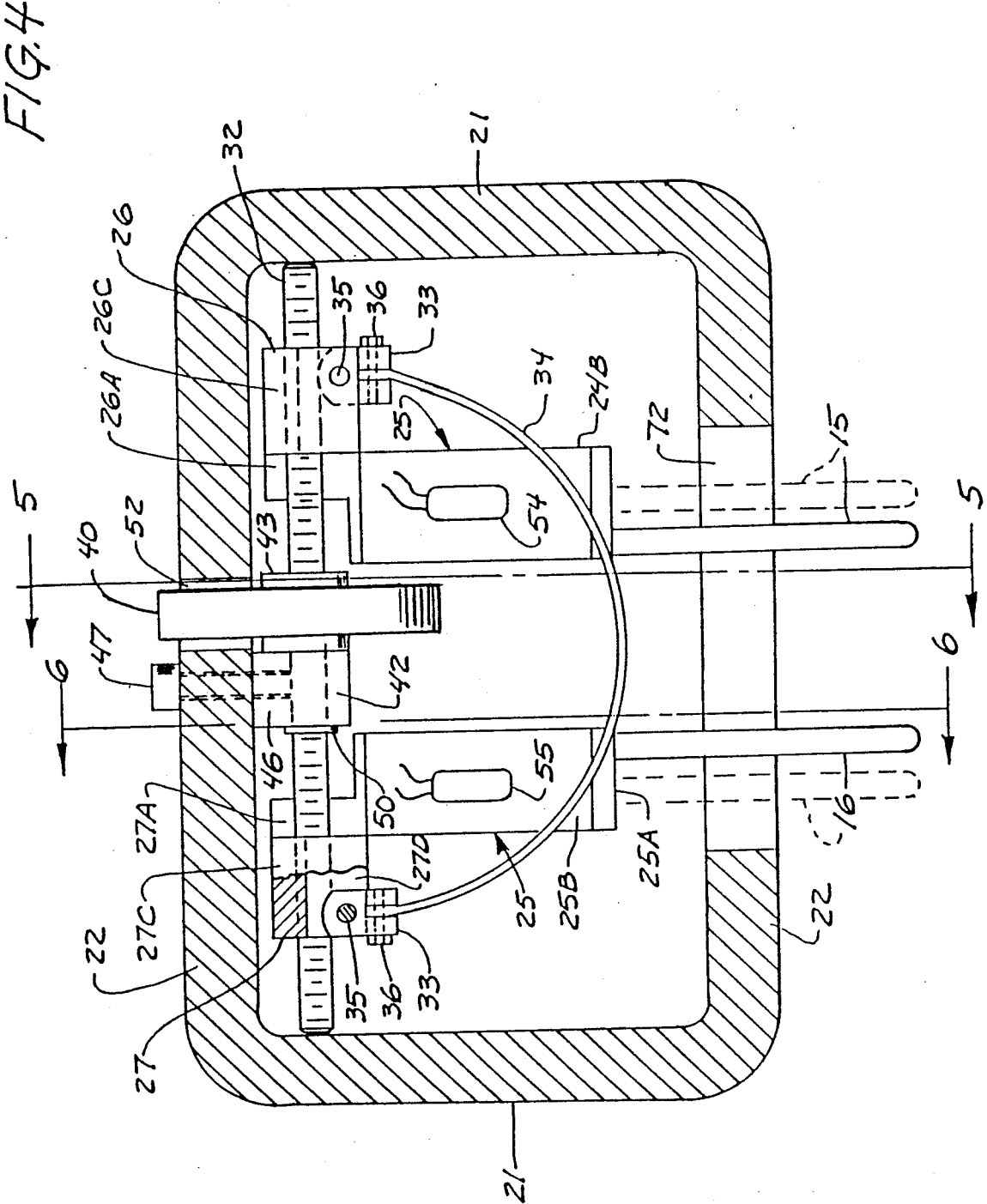
FIG. 4 is a top plan sectional view taken as on line 4—4 in FIG. 1.

The mounting block 42 has an upright column portion 46 which rests against a side wall of the case 11, as can be seen in FIG. 4, and the column 46 is held against the side wall of the case with a pair of cap screws 47 (see also FIGS. 3 and 5). The screws 47 positively locate and hold the support block 42, and thus the guide shaft 30 and threaded screw 32.

Additionally, the column 46 has an opening near the upper end in which a shank or shaft portion of the threaded member 32 is rotatably mounted. The threaded member 32 is held in position from endwise or axial movement in the opening in the column 46 through the use of a suitable retaining ring 50, and if desired, a washer can be placed between one side of this column and the thumb wheel 40 to keep the threaded screw 32 in position.

The side wall of the case supporting the mounting block 42 has a suitable slot indicated at 52 therein for permitting access for a person to rotate the thumb wheel. The top wall also has a slot 53 therein. A recess around the slot 53 provides access to the thumb wheel for moving it and rotating the threaded screw 32. The screw 32 has right and left hand threads on the opposite ends, so rotating the threaded screw 32 will cause driving of the column portions 26C and 27C of the slide and adjustment blocks toward or away from each other along shaft 30 within a range of movement. Note in FIG. 4 that the journal portions 26A and 27A are recessed to provide clearance for the center mounting block 42 so that the journals will move past the mounting block to position the prongs or pins 15 and 16 close together. The spring 34 resists spreading apart of the slide and adjustment blocks, and will urge them together.

The flexure straps 24B and 25B are relatively thin, and will flex easily when the respective prongs or pins are under load. The flexure of the members 24B and 25B is sensed through the use of strain gages illustrated schematically at 54 and 55, respectively. The strain gauges 54 and 55 can be mounted on both the upper and lower members 24B and 25B, so that a full wheatstone bridge can be provided with the strain gauges on these individual flexure straps. The loading is done by holding the case 10 and pressing the prongs against the finger surface.

FIG. 7 schematically shows a bridge 60 that is made up of strain gauges associated with the flexure straps 24B, and a bridge 61 that is made up of strain gauges associated with the flexure straps 25B. The bridges are excited from a common power source indicated at 62, and have output lines 60A and 61A, respectively, that are connected to a switching and conditioning circuit indicated at 64. This circuit 64 is used for permitting switching to provide an output along a line 65 from the bridge 60, or selectively an output along the line 66 from the bridge 61, or, if desired, an average output from the two bridges 60 and 61 along a line 67. The lines 65, 66 and 67 can be connected to a conventional readout circuit 70 that will read out in either pounds of force, or if desired deflection. The lines 65, 66 and 67 may be two or more individual wires and are shown schematically.

It should be noted that the prongs 15 and 16 extend out through a slot 72 in a side wall of the case, and that the upper surface 72A defining the slot 72 provides a mechanical stop against excessive deflection upwardly under load of the prongs.

The moving two point discrimination test will evaluate the innervation density of the quickly adapting fiber-receptor system, and when the moving test is to be conducted, the prongs 15 and 16 are set at a desired spacing, depending on the test, and the tips 15A and 16A are dragged along the surface of a finger or other portion of the human body, under a desired load. The moving two point discrimination test is done with the prongs being placed at the level of the distal interphalangeal joint and then moved slowly toward the tip of the finger, if a finger is being tested. Thus the prongs move from the proximal to the distal ends of the tip of the finger. The prongs are placed so that the line between the prong tips is exactly perpendicular to the long axis of the finger. This moving test can only be done when the two points stimulate different areas, but areas which are adjacent to each other. As most fingers are not wider than 12 to 14 millimeters, if a person cannot distinguish two moving points at such distances, the test is completed and no larger values are recorded, unless a larger surface such as a toe or dorsal radial aspect of the hand is being tested.

The load can be maintained by observing the readout circuit, because of the continuous monitoring of loads that are exerted. A substantially uniform force can be applied as the prongs are moved and the sensation can be described by the patient.

The static two point discrimination test, which evaluates the innervation density of the slowly adapting fiber-receptor system, is conducted by moving the prongs into contact with the portion of the hand and then pressing until a sensation is felt by the patient.

For the static two point discrimination test, the prongs are also held so that the line between the tips is perpendicular to the long axis of the finger, and then a pressure is exerted by holding the case and permitting the flexure straps 24B and 25B to flex. If the fact that there are two points engaging the finger cannot be observed by the patient within the width of the finger, the prongs can be placed so that they are parallel to the long axis of the finger. The spacing of the prongs can be changed as desired.

Generally speaking, the prongs are placed on the skin only with sufficient pressure for a patient to determine that there is stimulation without causing pain. With some nerve problems, such as early in the course of neural regeneration or with advanced nerve compression, when the threshold for sensory stimuli is greatly increased, the prongs must be pressed into the surface of the finger with greater force so that the stimulus is perceived. Sometimes the patient will indicate that the prongs feel as "one wide point", which indicates that the discrimination level of load is being approached. Alternating between one and two point tests also can be done so that the patient is aided in discriminating between the two separate points of force application. The device of the present invention can be used for diagnosing nerve injury, and evaluating nerve repair progress. It provides for a range of adjustment necessary to accommodate most patients, and by providing a force or load reading, either for each prong individually or as an average, it can be applied in a wide variety of situations, where only one prong is used, or both prongs are used. The prongs or pins 15 and 16 are sufficiently rigid to transfer the loading to the flexures that support them.

Although the present invention has been described with reference to preferred embodiments, workers skilled in the art will recognize that changes may be made in form and detail without departing from the spirit and scope of the invention.

What is claimed is:

1. A testing apparatus for sensory perception of a skin of a human comprising a support member, a prong, means connecting said prong to said support member comprising a load determining assembly, the load determining assembly having a pair of spaced parallel flexure straps with first ends thereof attached to the support member, and a connector at the second ends thereof, said connector mounting said prong, the load determining assembly measuring the load applied in a selected direction at the outer end of the prong.

2. The apparatus as specified in claim 1 and a housing supporting said support member, a second prong, and means for connecting said second prong to said support member comprising a second load determining assembly, the second load determining assembly measuring the load applied to the second prong in a selected direction at the outer end of the second prong independently of the first mentioned means.

3. The apparatus as specified in claim 2 wherein said support member comprises a pair of transversely movable slide and adjustment blocks, means for mounting said pair to a guide such that said slide and adjustment blocks are capable of sliding movement toward and away from each other, and means for adjusting the position of said blocks relative to each other.

4. The apparatus as specified in claim 3 wherein said means for adjusting the position comprises screw means for operably engaging both of said blocks.

5. The apparatus as specified in claim 4 and spring means urging said blocks to move together, said urging being resisted by said screw means.

6. A testing apparatus for sensory preception of a skin of a human comprising a support member, a prong having a prong axis, and a load determining assembly comprising a pair of flexure straps having first ends and second ends defining longitudinal lengths, the first ends attached to the support member and the prong mounted to the second ends with the prong axis perpendicular to the longitudinal lengths of the straps, and force measurement means on at least one strap, the force measurement means measuring a force applied at an outer end of the prong in a selected direction.

7. The apparatus as specified in claim 6 and a second prong connected to said support member with a second load determining assembly, wherein said support member comprises a pair of transversely movable slide and adjustment blocks, means for mounting said pair to a guide such that said slide and adjustment blocks are capable of sliding movement toward and away from each other, and means for adjusting the position of said blocks relative to each other.

8. A method of testing sensory perception of a human patient comprising the steps of:
  providing two prongs with exposed tips that are spaced apart a selected distance each prong being mounted to a housing through spaced parallel flexure straps with means for measuring a load at each prong mounted thereon;
  determining a preselected load to be applied to the tips of the prongs;
  simultaneously pressing the tips of the prongs against the skin to be tested; and
  moving the prongs over the surface of the skin while maintaining the preselected load to determine perception of the patient.

* * * * *